(12) United States Patent
Biondolillo (10) Patent No.: US 8,100,876 B1
(45) Date of Patent: Jan. 24, 2012

(54) UNDERGARMENTS WITH SANITARY ABSORBENT DEVICE HOLDER

(76) Inventor: Kathy Biondolillo, Parkland, FL (US)

( * ) Notice: Subject to any disclaimer, the term of this patent is extended or adjusted under 35 U.S.C. 154(b) by 449 days.

(21) Appl. No.: 12/123,579

(22) Filed: May 20, 2008

(51) Int. Cl.
*A61F 13/15* (2006.01)

(52) U.S. Cl. ............ 604/385.14; 604/386; 604/387; 604/393; 604/385.19; 604/396; 604/385.13; 604/385.02

(58) Field of Classification Search .......... 604/385.14, 604/386, 387, 385.19, 396, 393, 385.13, 604/385.02
See application file for complete search history.

(56) References Cited

U.S. PATENT DOCUMENTS

| 6,076,195 A | 6/2000 | Klein |
| 6,308,340 B1 | 10/2001 | Cook |
| 6,772,446 B1 | 8/2004 | Black |
| 2003/0199844 A1 * | 10/2003 | LaVon et al. ............ 604/385.14 |

\* cited by examiner

*Primary Examiner* — Jacqueline F Stephens
(74) *Attorney, Agent, or Firm* — Gold & Rizvi, P.A.; Glenn E. Gold; H. John Rizvi (57) ABSTRACT

Undergarments with sanitary absorbent device holders include an undergarment body and a sanitary absorbent device holder carried by the undergarment body. The sanitary absorbent device holder is adapted to hold a sanitary absorbent device such as a tampon or sanitary napkin in a discreet or concealed manner as the undergarment is worn by a user.

21 Claims, 10 Drawing Sheets

UNDERGARMENTS WITH SANITARY ABSORBENT DEVICE HOLDER

BACKGROUND OF THE INVENTION

1. Field of the Invention

The present invention relates to undergarments. More particularly, the present invention relates to an undergarment having a pocket that is adapted to hold a sanitary absorbent device such as a tampon or sanitary napkin in a discreet or concealed manner.

2. Discussion of the Related Art

Women frequently carry sanitary absorbent devices such as tampons and/or sanitary napkins so that the devices will be available when needed. These devices are typically stored and carried in a discreet or concealed manner such as in a purse or handbag, which the woman carries, for example. However, a purse may be undesirable to store and carry the devices since the tampons and/or sanitary napkins may occupy excessive space and/or contribute to disorganization of the contents of the purse. Furthermore, carrying a purse can be less than ideal at certain events, functions, schools, nightclubs, and work environments. Examples of potential occupations or events include: nursing/medical profession, clerks, cashiers, flight attendants, bar tenders, dancers, bikers, aerobics, stadium events, concerts, servers, young adolescents in school, executive meetings, etc., and the like.

Several teachings are known, placing a pocket on an inside of an undergarment. Placing items into a pocket on the inside of an undergarment can be uncomfortable. A woman's undergarment is normally designed for a tight fit. An object placed in a pocket located inside the undergarment is pressed against the wearer's body by the tight fitting garment causing discomfort. Furthermore, the internal pocket location hampers access to items placed inside the pocket, as the user is required to stretch the waistband outward.

Another teaching places pockets centered about each side of an undergarment. It is normally undesirable to place objects on the sides of one's body for many reasons. One example is a person's side is very susceptible to accidentally hitting an object. Another is the small radius of the curve about one's hip is not conducive to accessing an object within a side pocket. The tight curve tends to keep the pocket closed. Long objects that are not conducive to the natural bends of the human body, such as guns and knives, are placed along one's side for ease of access for use and ability to compensate for the natural bends.

Therefore, undergarments are needed which are fitted with holders suitable for holding a sanitary device such as a tampon or sanitary napkin in a discreet or concealed and comfortable manner.

SUMMARY OF THE INVENTION

The present invention is generally directed to undergarments, which are fitted with holders suitable for holding a sanitary device such as a tampon or sanitary napkin in a discreet or concealed manner. Each undergarment may be comfortably and discreetly worn by a user and hold a sanitary absorbent device such as a tampon or sanitary napkin in a secure and accessible manner.

In one aspect of the invention, the undergarment comprises:
an undergarment body; and
a sanitary absorbent device holder carried by the undergarment body.

In another aspect of the invention, the sanitary absorbent device holder may include a tampon pocket sized and configured to receive at least one tampon.

In still another aspect of the invention, the sanitary absorbent device holder may include a sanitary napkin pocket sized and configured to receive at least one sanitary napkin. This pocket could also be used to hold other material or items.

In yet another aspect of the invention, the sanitary absorbent device holder may include a pair of spaced-apart elastic bands sized and configured to receive a tampon.

In a still further aspect of the invention, the sanitary absorbent device holder may include a scroll pocket sized and configured to receive a tampon.

In another aspect of the invention, a cover panel may be carried by the undergarment body and conceal the sanitary absorbent device holder.

In yet another aspect of the invention, the sanitary absorbent device holder may be carried by the cover panel.

In still another aspect of the invention, a closure mechanism may be carried by the undergarment body and the sanitary absorbent device holder.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION OF REPRESENTATIVE EMBODIMENTS

Shown throughout the Figures, the present invention is generally directed to undergarments that are fitted with holders suitable for holding a sanitary device such as a tampon or sanitary napkin in a discreet or concealed manner. Each undergarment may be comfortably and discreetly worn by a user and hold a sanitary absorbent device, such as a tampon or sanitary napkin, in a secure and accessible manner.

Figure 1:
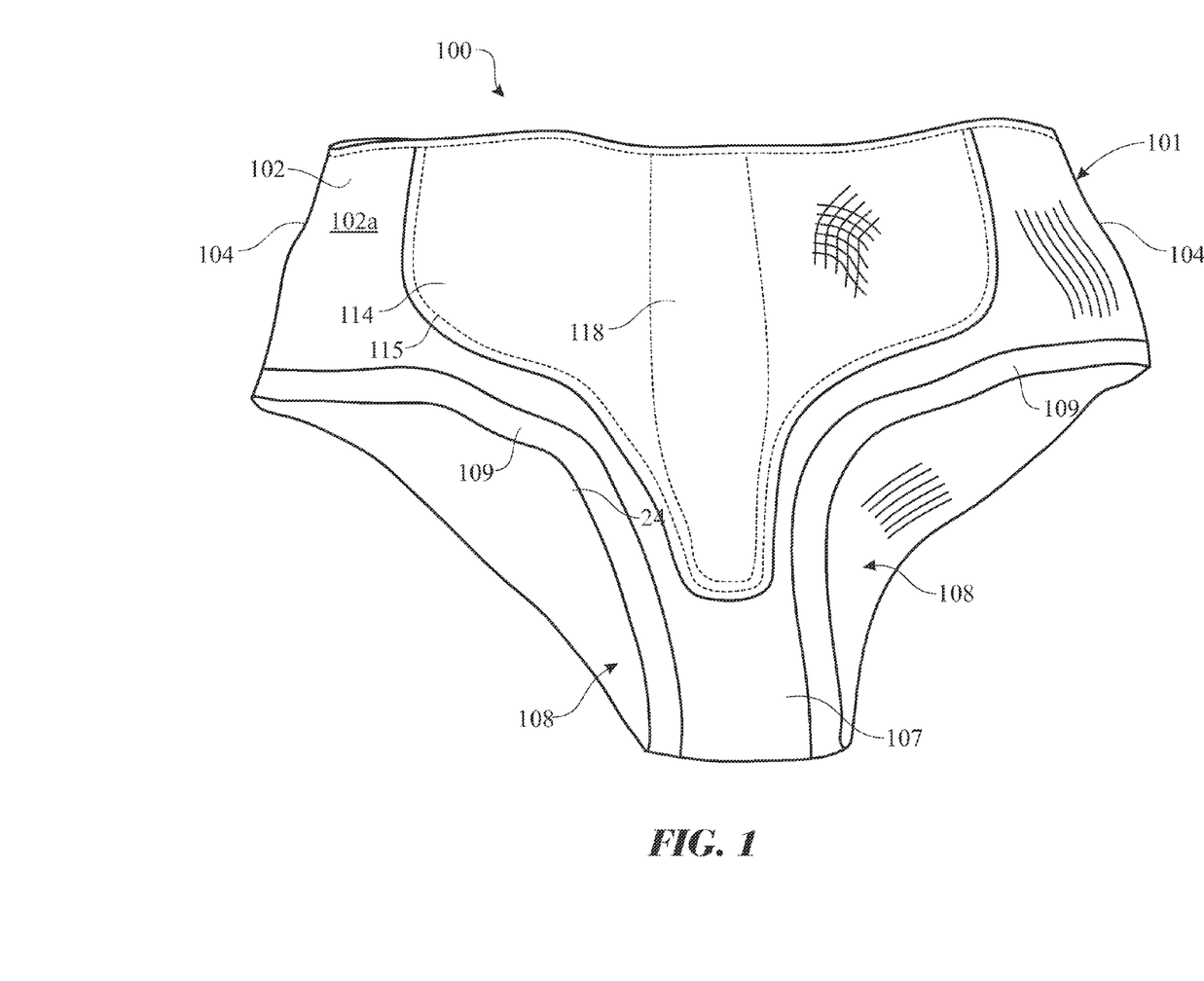
FIG. 1 is a front view of an illustrative embodiment of the undergarments with sanitary absorbent device holder, with a vertically-oriented tampon pocket provided on the undergarment.
Figure 2:
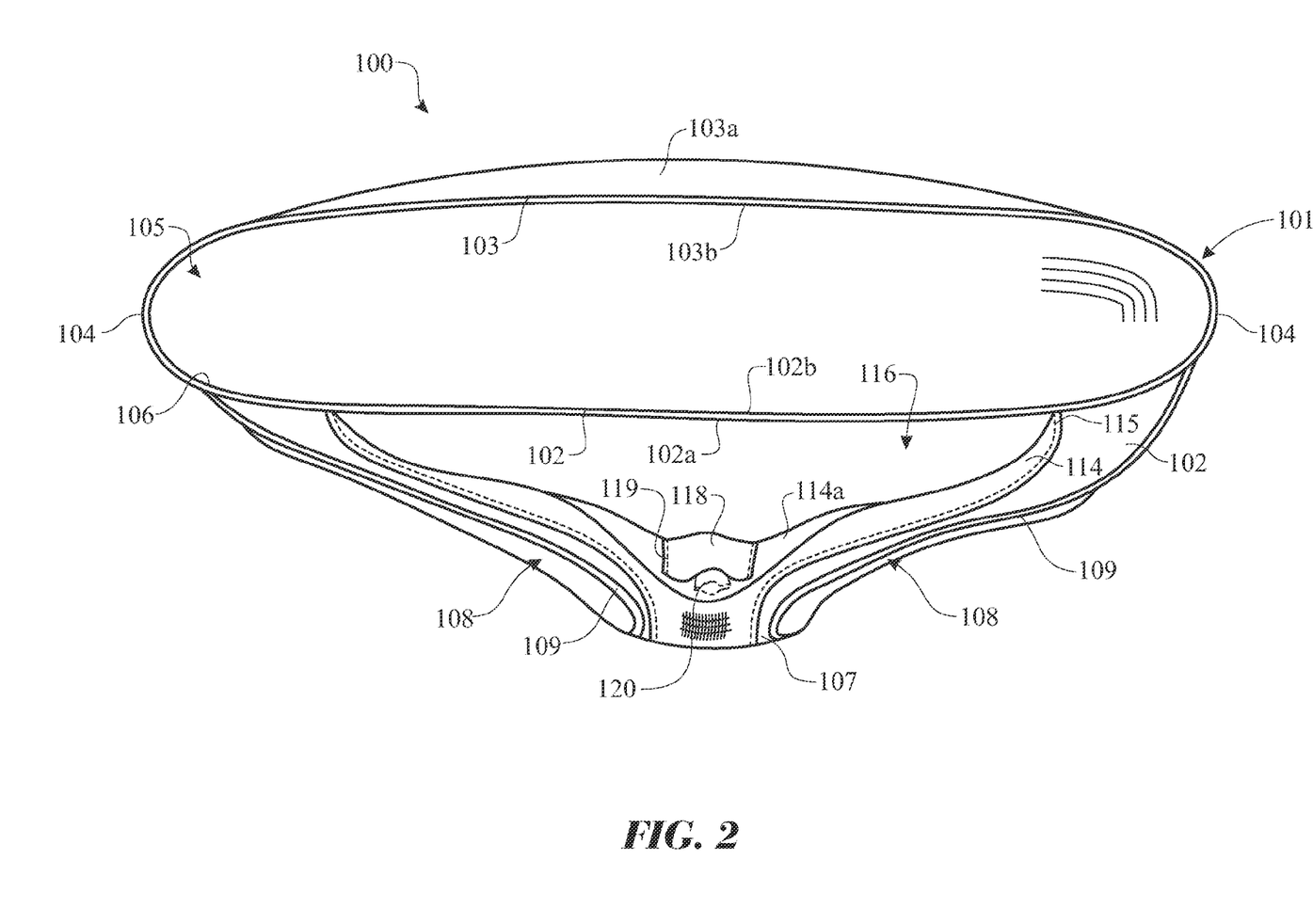
FIG. 2 is a top perspective view of an illustrative embodiment of the undergarment with sanitary absorbent device holder, with a tampon (shown in phantom) inserted in a tampon pocket provided on the undergarment.

Referring initially to FIGS. 1 and 2 of the drawings, an illustrative embodiment of the undergarments with sanitary absorbent device holder, hereinafter undergarment, is generally indicated by reference numeral 100. The undergarment 100 includes an undergarment body 101 which may be any suitable size and material such as cotton, polyester or cotton/polyester blend, for example. The undergarment body 101 may be any style of undergarment including but not limited to briefs, boxer shorts, bikini or thong. The undergarment body 101 may include a front body (anterior) portion 102, a rear body (posterior) portion 103 and side body portions 104 which connect the front body portion 102 and the rear body portion 103 and has a waist opening 105, as illustrated in FIG. 2. As further illustrated in FIG. 2, the front body portion 102 has an exterior surface 102a and an interior surface 102b. The rear body portion 103 has an exterior surface 103a and an interior surface 103b.

A crotch portion 107 may connect the front body portion 102 and the rear body portion 103. Leg openings 108 may be defined by the front body portion 102, the rear body portion 103, the side body portions 104, and the crotch portion 107. An elastic leg band 109 may circumscribe each leg opening 108.

A pocket cover panel 114 is provided on the undergarment body 101. In some embodiments, the pocket cover panel 114 may be provided on the front body portion 102 of the undergarment body 101. In the embodiment illustrated in FIGS. 1 and 2, the pocket cover panel 114 is provided on the exterior surface 102a of the front body portion 102; however, in other embodiments the pocket cover panel 114 may be provided on the interior surface 102b of the front body portion 102 or in any other suitable location on the undergarment body 101. The pocket cover panel 114 may be attached to the undergarment body 101 by cover panel stitching 115 or other suitable attachment technique. Although the illustrated exemplary embodiment shows a free formed pocket cover panel 114, it is recognized the pocket cover panel 114 can be shaped to conform to seams of the undergarment body 101. As illustrated in FIG. 2, the pocket cover panel 114 has a cover panel interior 116. A cover panel interior surface 114a of the pocket cover panel 114 faces the cover panel interior 116.

A generally elongated tampon pocket 118 (shown in phantom in FIG. 1) is provided on the cover panel interior surface 114a of the pocket cover panel 114, or alternatively, on the exterior surface 102a of the front body portion 102 in the cover panel interior 116 of the pocket cover panel 114. The tampon pocket 118 may be attached to the pocket cover panel 114 by pocket stitching 119 or other suitable attachment technique. As illustrated in FIG. 1, in some embodiments a longitudinal axis of the tampon pocket 118 may be oriented in generally perpendicular relationship with respect to a longitudinal axis of the undergarment body 101. The tampon pocket 118 is sized to contain at least one tampon 120 (shown in phantom in FIG. 2).

In typical use, the undergarment 1 is donned by a female wearer (not illustrated) and worn beneath the outer clothing (not illustrated) of the wearer. At least one tampon 120 (FIG. 2) is inserted in the tampon pocket 118 in the cover panel interior 116 of the pocket cover panel 114. When use of the tampon 120 is necessary, the wearer of the undergarment can easily remove the tampon 120 from the tampon pocket 118. It will be appreciated by those skilled in the art that the tampon 120 is discreetly and securely concealed in the tampon pocket 118 as the wearer wears the undergarment 100.

Figure 3:
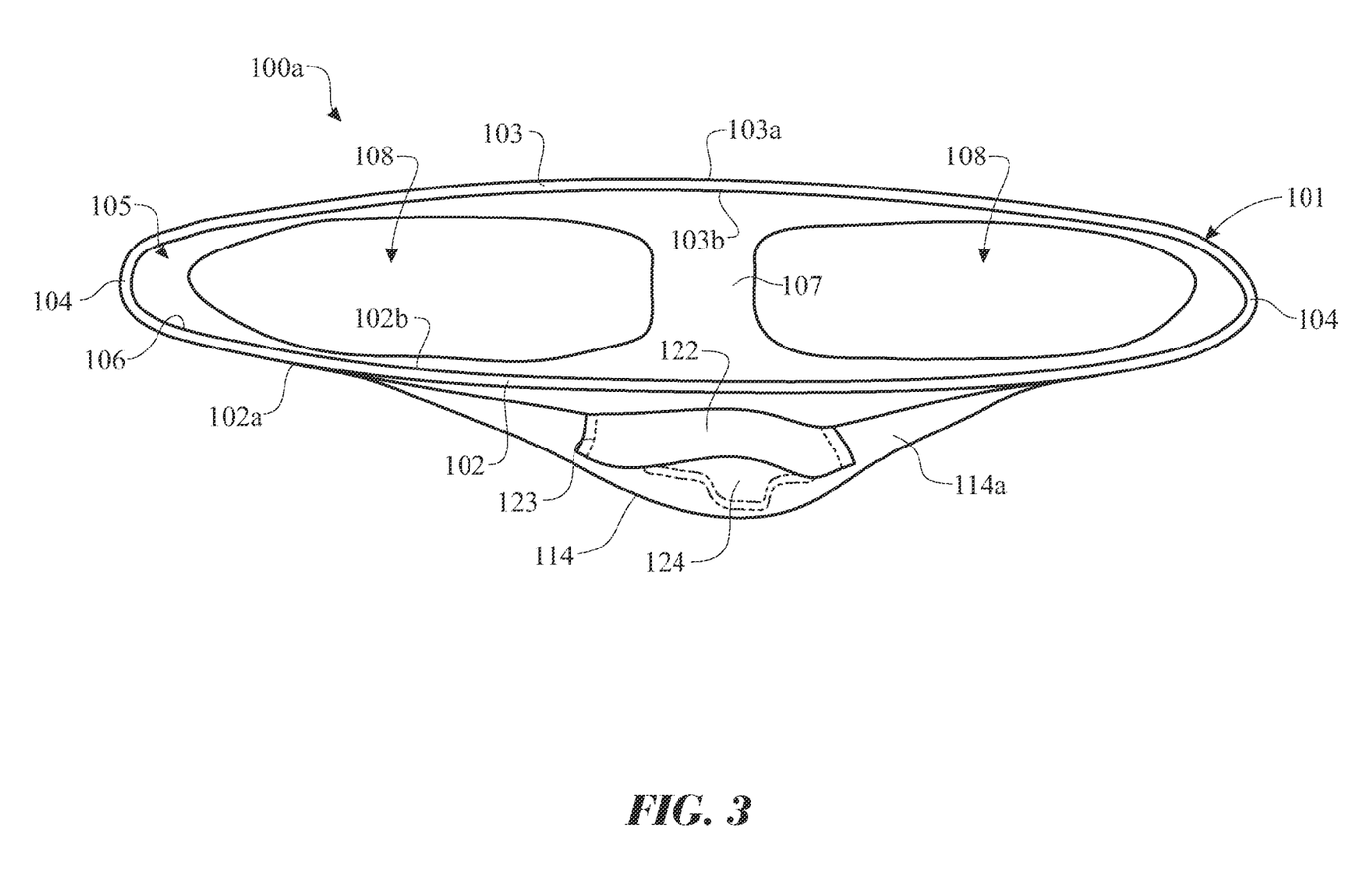
FIG. 3 is a top perspective view of another illustrative embodiment of the undergarment with sanitary absorbent device holder, with a sanitary napkin (shown in phantom) inserted in a sanitary napkin pocket provided on the undergarment.

Referring next to FIG. 3 of the drawings, another illustrative embodiment of the undergarment 100a includes a sanitary napkin pocket 122, which is attached to the cover panel interior surface 114a of the cover panel 114 such as by pocket stitching 123, for example. The sanitary napkin pocket 122 may have a generally elongated configuration and may be oriented in generally perpendicular relationship with respect to the longitudinal axis of the undergarment body 101. Accordingly, the sanitary napkin pocket 122 is sized to receive and conceal a sanitary napkin 124 until use of the sanitary napkin 124 is necessary.

Figure 4:
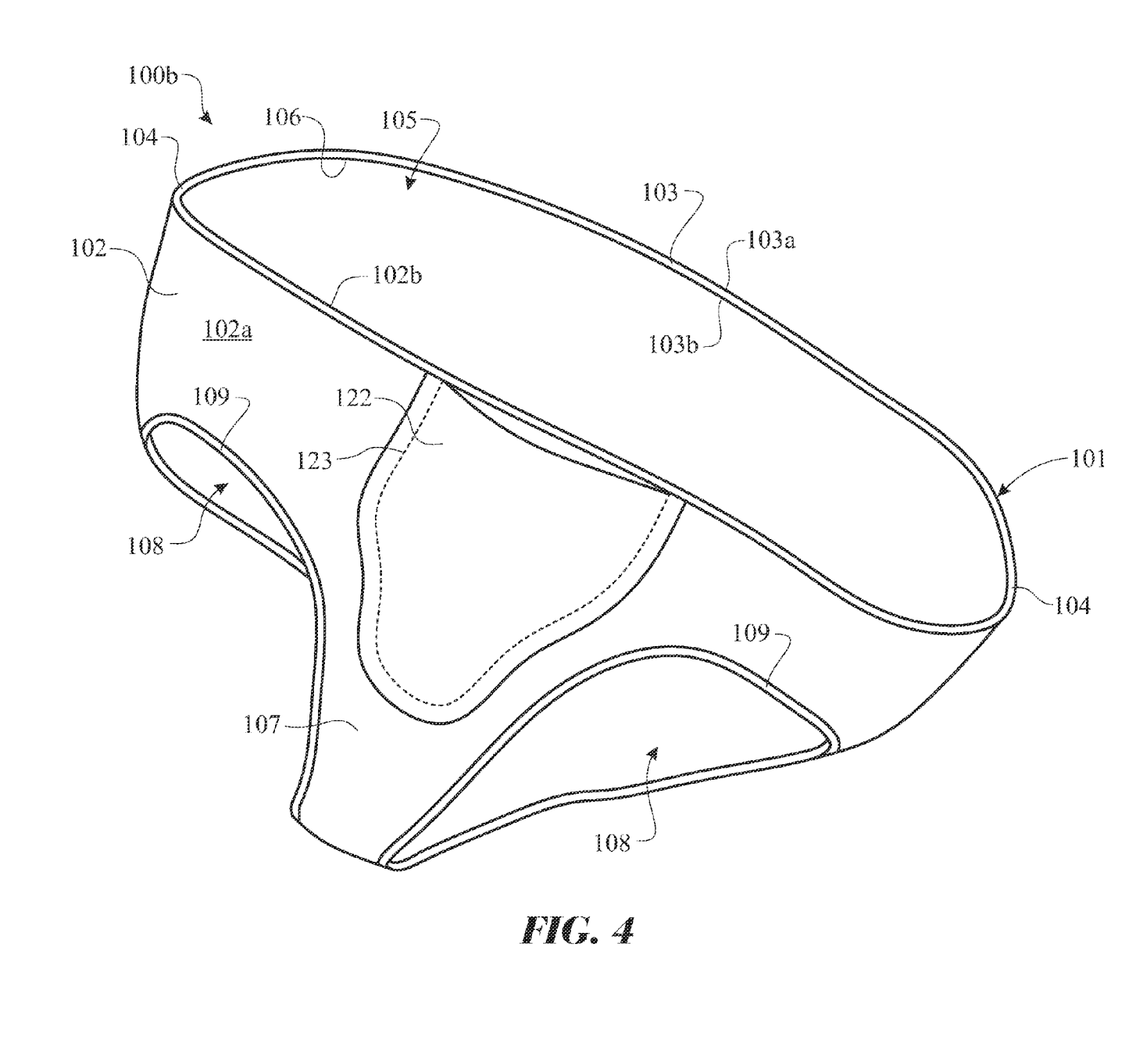
FIG. 4 is a front perspective view of another illustrative embodiment of the undergarment with sanitary absorbent device holder, with a sanitary napkin pocket provided on the exterior of the undergarment.
Figure 5:
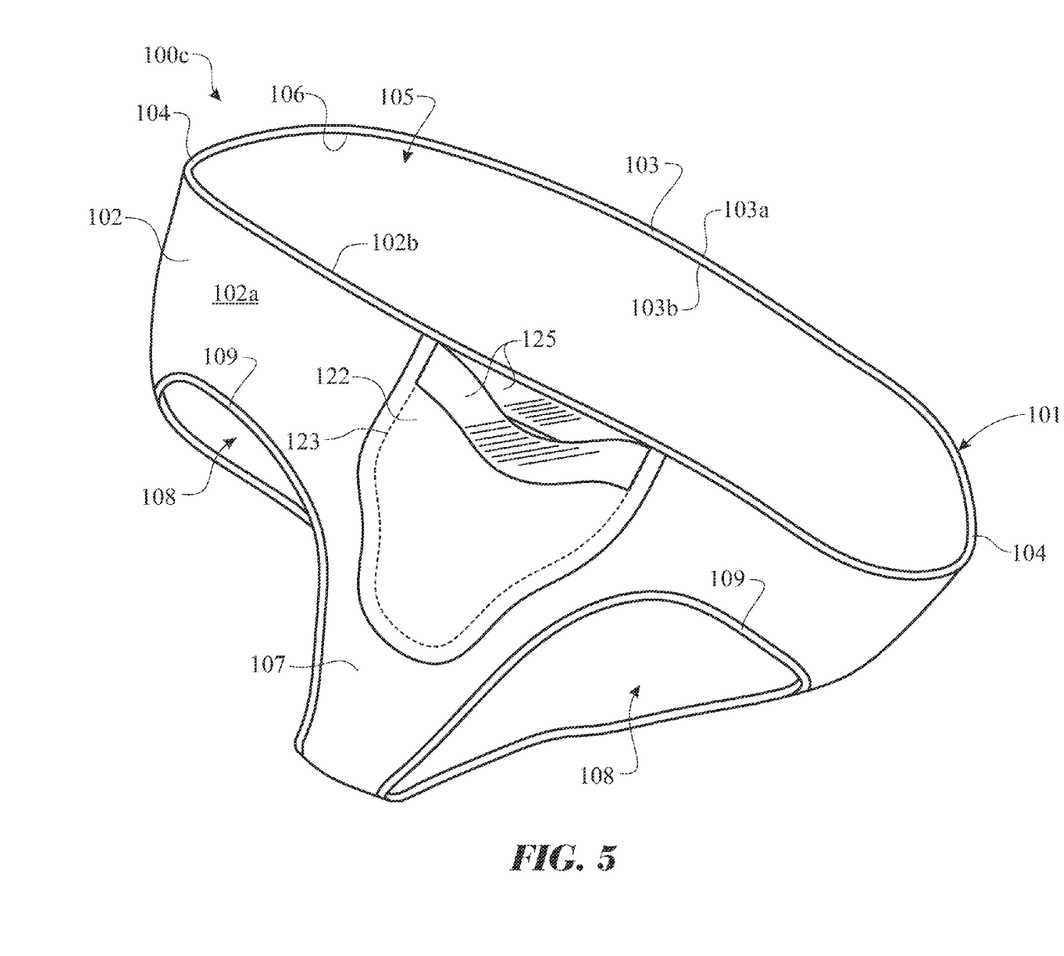
FIG. 5 is a front perspective view of another illustrative embodiment of the undergarment with sanitary absorbent device holder, with a sanitary napkin pocket provided on the exterior of the undergarment and provided with a closure strip.
Figure 6:
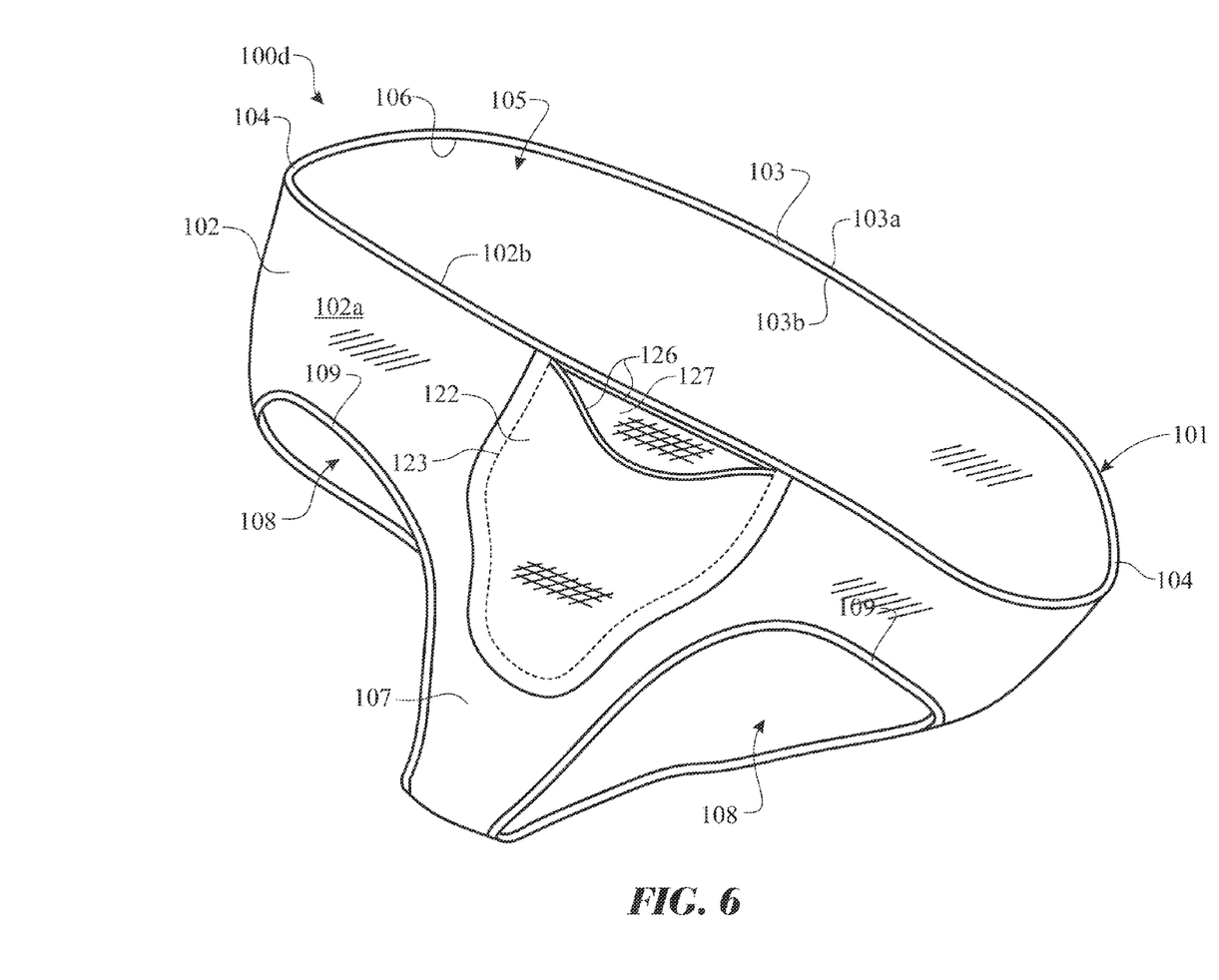
FIG. 6 is a front perspective view of another illustrative embodiment of the undergarment with sanitary absorbent device holder, with a sanitary absorbent device pocket provided on the exterior of the undergarment and provided with an alternative, interlocking closure strip.

Referring next to FIGS. 4-6 of the drawings, in another illustrative embodiment of the undergarment 100b illustrated in FIG. 4, the pocket cover panel 114 (FIG. 3) may be omitted and the sanitary napkin pocket 122 is attached to the exterior surface 102a of the front body portion 102 or to any other suitable location on the undergarment body 101. In another illustrative embodiment of the undergarment 100c illustrated in FIG. 5, a closure mechanism 125 is provided on the sanitary napkin pocket 122 and the undergarment body 101, respectively, to secure the sanitary napkin pocket 122 in a closed configuration. The closure mechanism 125 may be complementary hook and loop fasteners, a zipper, snap(s), button(s) or a frog-style enclosure (lace with a knot or button), for example and without limitation. In another illustrative embodiment of the undergarment 100d illustrated in FIG. 6, a pair of complementary interlocking closure strips 126 is provided on the sanitary napkin pocket 122 and the undergarment body 101, respectively, to seal the sanitary napkin 124 (FIG. 3) in the sanitary napkin pocket 122. A waterproof pocket liner 127 may line the interior surfaces of the sanitary napkin pocket 122.

Figure 7:
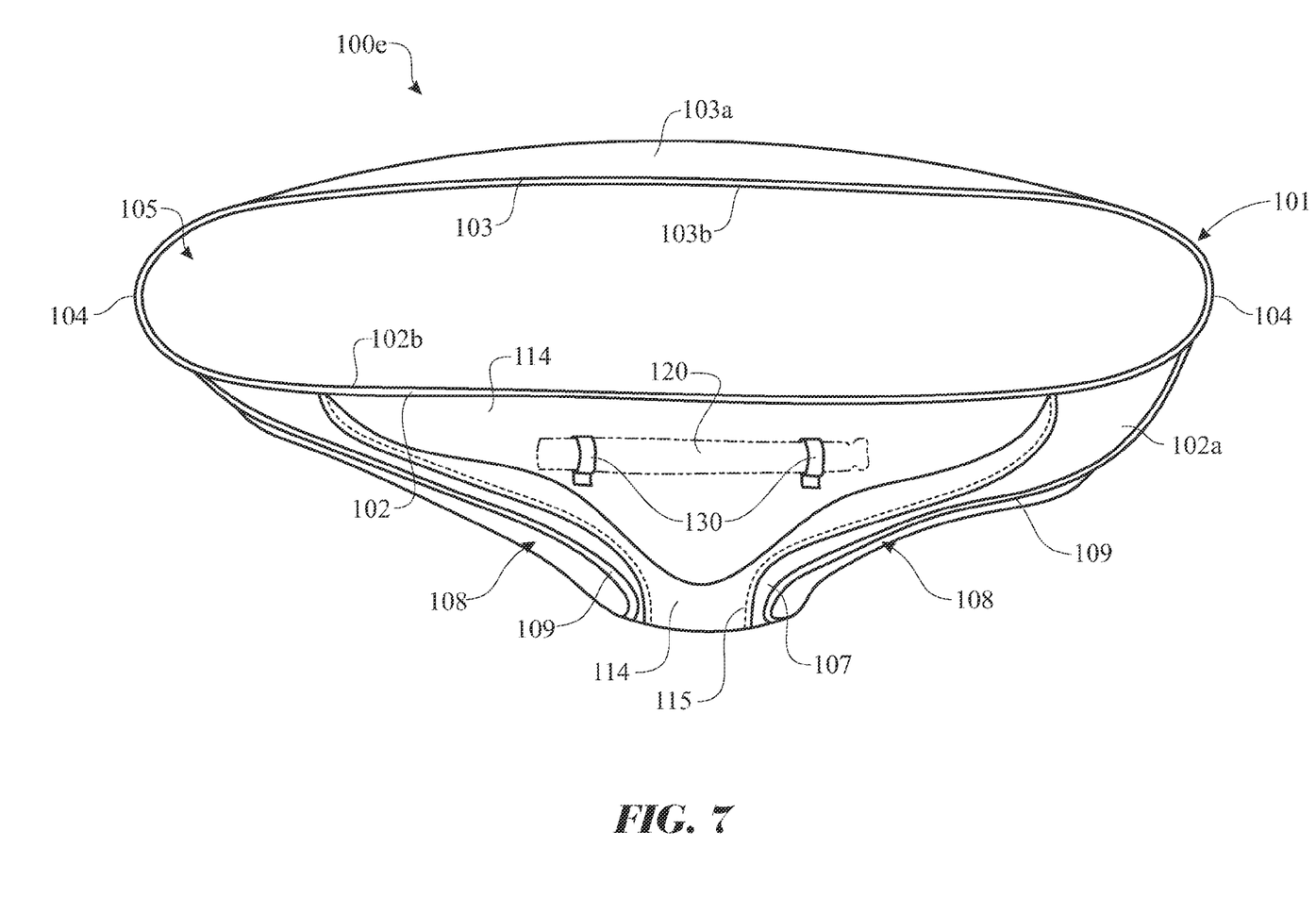
FIG. 7 is a top perspective view of another illustrative embodiment of the undergarment with sanitary absorbent device holder, with a pair of spaced-apart elastic bands provided on the undergarment and adapted to hold a tampon (shown in phantom)

Referring next to FIG. 7 of the drawings, in another illustrative embodiment of the undergarment 100e, a pair of spaced-apart elastic bands 130 is provided on the exterior surface 102a of the front body portion 102 or in any other suitable location on the undergarment body 101. The elastic bands 130 may be sewn or otherwise attached to the front body portion 102 using any suitable alternative technique known by those skilled in the art. A tampon 120 (shown in phantom) can be removably inserted in the elastic bands 130. In some embodiments, a pocket cover panel 114 may be attached to the undergarment body 101 to cover and conceal the elastic bands 130 and the tampon 120. In other embodiments, the elastic bands 130 can alternately be positioned along the sides or rear of the undergarment body 101, top or middle of the undergarment body 101. A frog style closure, ribbon, ribbon or similar device can be deployed to attach or anchor the tampon 120 anywhere within the undergarment. The bands 130 can be oriented such to optimize the configuration. An example would be orienting the bands 130 such to contain the tampon 120 vertically when provided on a side of the undergarment body 101. It can also be placed vertically or horizontally on a rear of the undergarment body 101. A frog style closure, ribbon, or similar device can be deployed to attach or anchor the tampon 120 anywhere within the undergarment.

Figure 8:
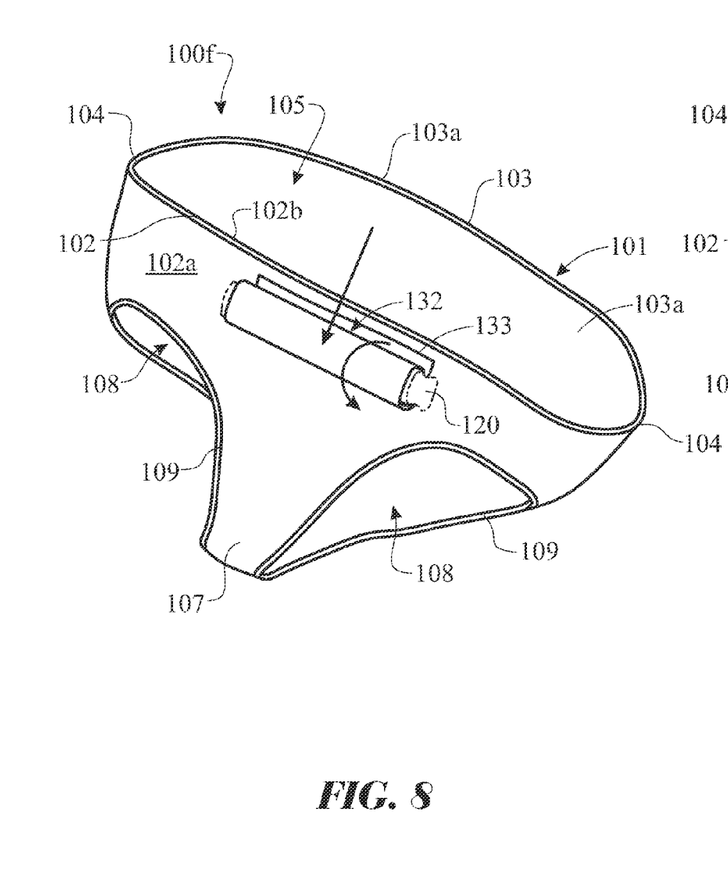
FIG. 8 is front perspective view of another illustrative embodiment of the undergarment with sanitary absorbent device holder, with a scroll pocket provided on the undergarment and a tampon (shown in phantom) secured in the rolled-up scroll pocket.
Figure 9:
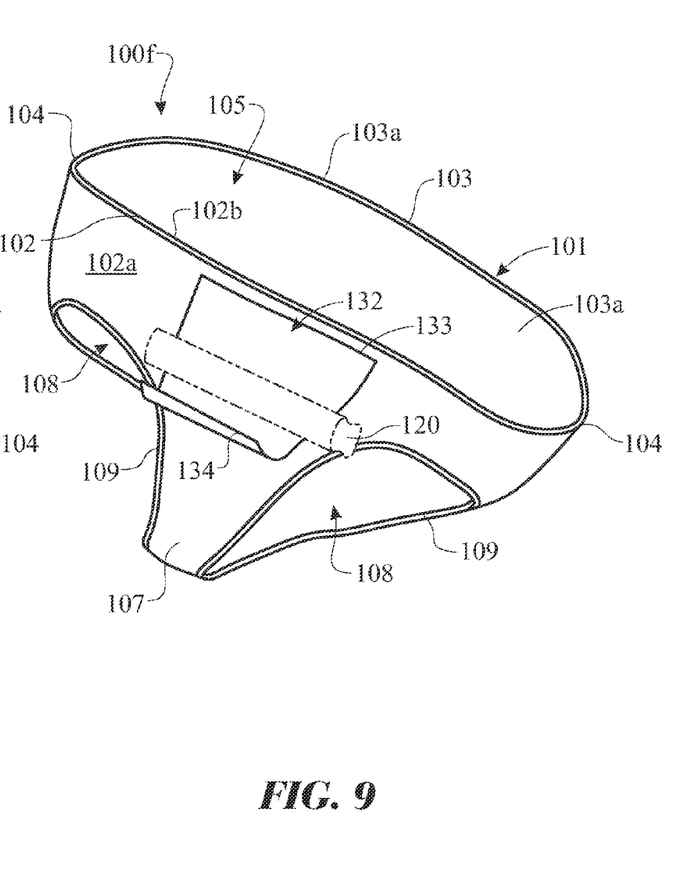
FIG. 9 is front perspective view of the undergarment with sanitary absorbent device holder illustrated in FIG. 8, with the scroll pocket shown in an unrolled, extended configuration.

Referring next to FIGS. 8 and 9 of the drawings, in another illustrative embodiment of the undergarment 100f, a generally elongated, flexible scroll pocket 132 is provided on the exterior surface 102a of the front body portion 102 or in any other suitable location on the undergarment body 101. The scroll pocket 132 may include, for example, an attachment edge 133 which is sewn or otherwise attached to the undergarment body 101 and a free edge 134, which is opposite the attachment edge 133. The scroll pocket 132 can be selectively deployed in a rolled configuration illustrated in FIG. 8, in which a tampon 120 can be secured and concealed in the rolled scroll pocket 132, and an extended or unrolled configuration illustrated in FIG. 9, in which the tampon 120 can be removed from the scroll pocket 132 for use.

Figure 10:
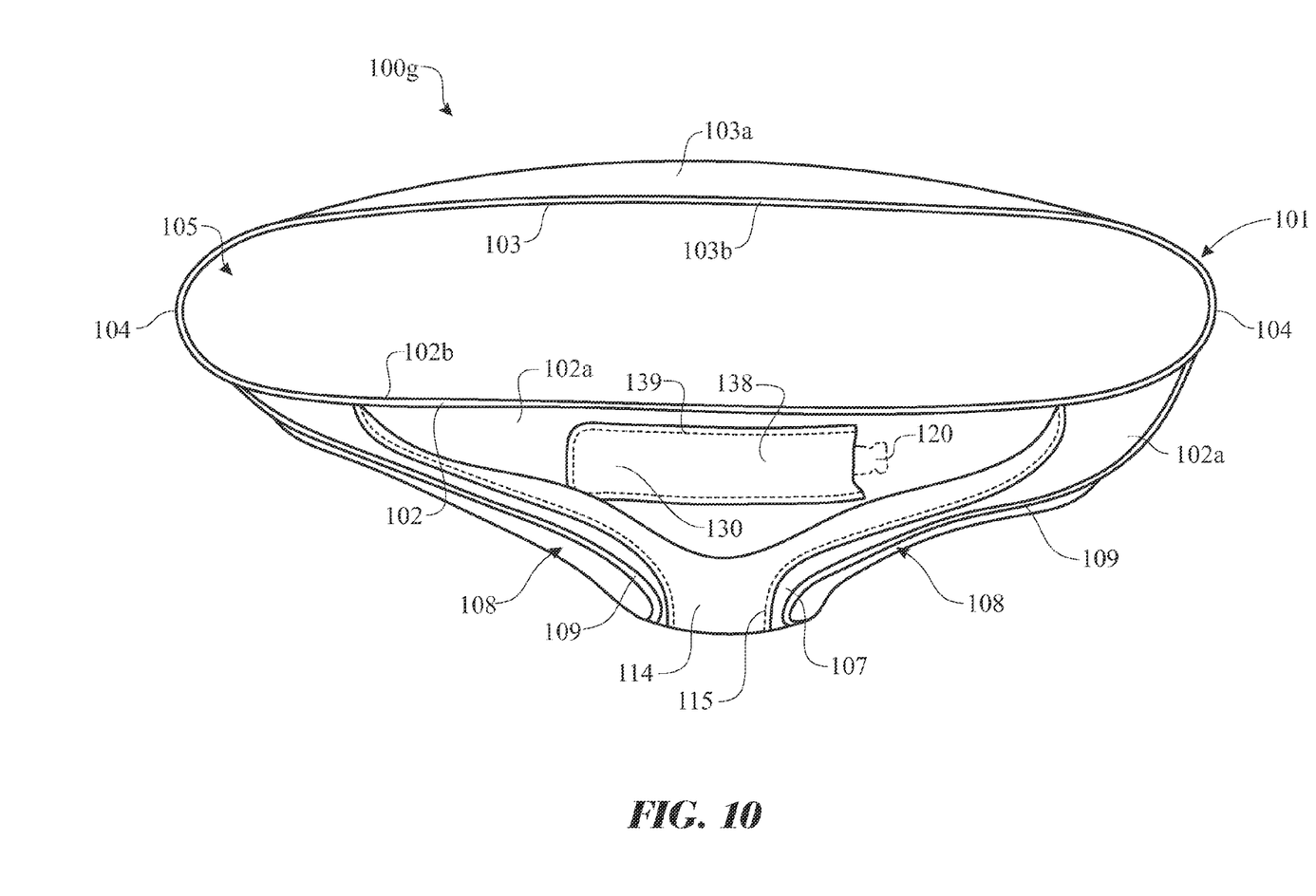
FIG. 10 is a top perspective view of another illustrative embodiment of the undergarment with sanitary absorbent device holder, illustrating a laterally-oriented tampon pocket provided on the undergarment.

Referring next to FIG. 10 of the drawings, in another illustrative embodiment of the undergarment 100g, a generally elongated tampon pocket 138 is attached to the exterior surface 102a of the front body portion 102 or any other suitable location on the undergarment body 101 such as by pocket stitching 139, for example. The longitudinal axis of the tampon pocket 138 may be oriented in generally parallel relationship with respect to the longitudinal axis of the undergarment body 101. A pocket cover panel 114 may be provided on the undergarment body 101 to conceal the tampon pocket 138.

Figure 11:
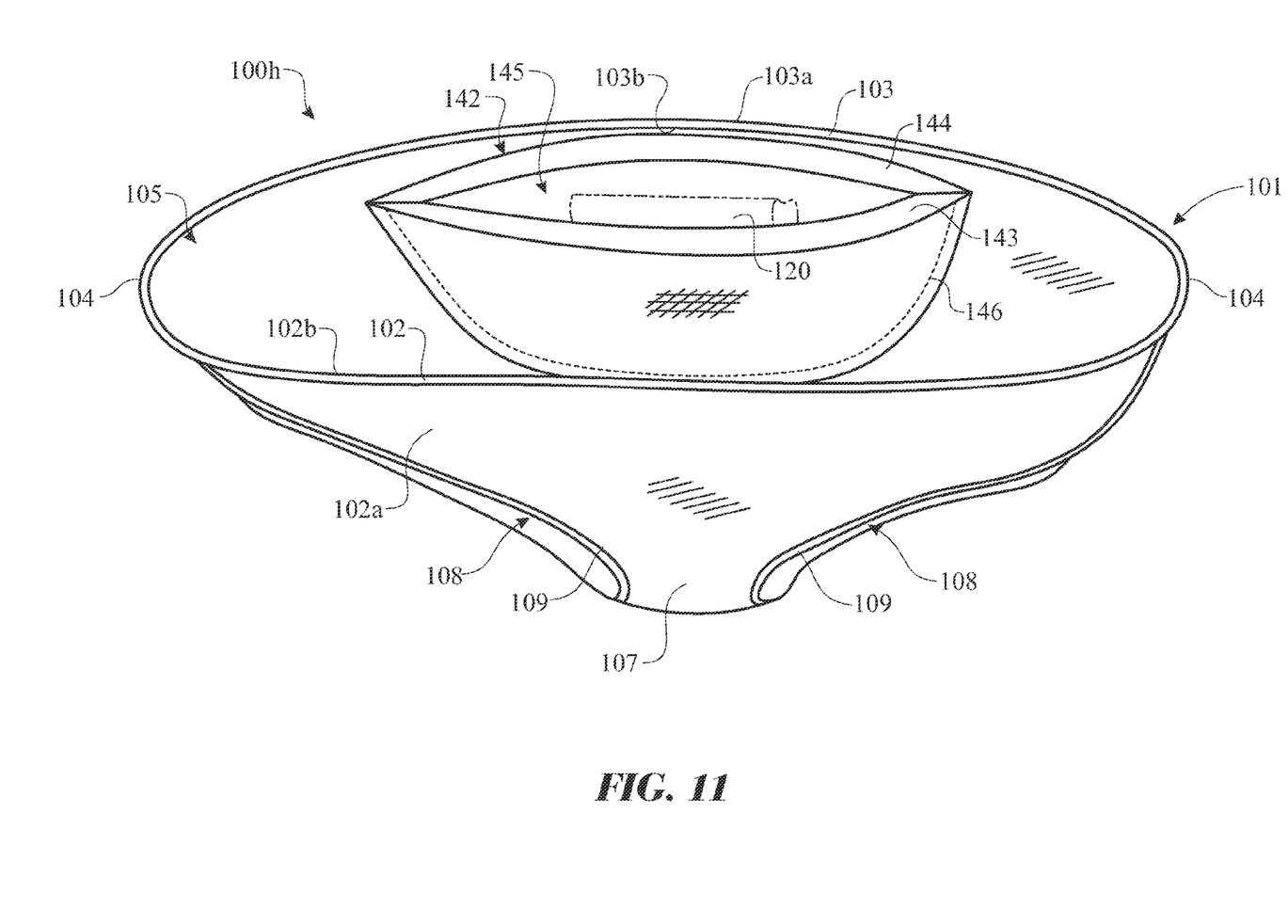
FIG. 11 is a top perspective view of another illustrative embodiment of the undergarment with sanitary absorbent device holder, with a tampon pocket provided in the interior of the undergarment.

Referring next to FIG. 11 of the drawings, in another illustrative embodiment of the undergarment 100h, a sanitary absorbent device compartment 142 is provided in the undergarment body 101. The sanitary absorbent device compartment 142 may include a rear compartment panel 144 which is sewn or otherwise attached to the interior surface 103b of the rear body portion 103. A front compartment panel 143 may be sewn to the rear compartment panel 144 by compartment stitching 146 or may be otherwise attached to the rear compartment panel 144. The front compartment panel 143 and the rear compartment panel 144 define a compartment interior 145. Accordingly, one or multiple sanitary absorbent devices such as a tampon 120 (shown in phantom) and/or sanitary napkins 124 (FIG. 3) may be placed and concealed in the compartment interior 145 of the sanitary absorbent device compartment 142 until use is needed. In other embodiments, the sanitary absorbent device compartment 142 may be attached to the exterior surface 103a of the rear body portion 103; to the exterior surface 102a or the interior surface 102b of the front body portion 102; or to any suitable alternative location on the undergarment body 101.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

I claim:

1. An undergarment adapted to discreetly store a packaged sanitary absorbent article, the undergarment comprising:
    a unitary liquid pervious undergarment main body constructed to be worn about a lower torso portion of a human body, said undergarment main body having interior and exterior surfaces and contiguous front and rear portions forming a waist-receiving opening and a pair of leg-receiving openings, said waist receiving opening defined by an upper edge of said undergarment main body;
    a cover panel attached to said exterior surface of said undergarment main body, said cover panel having a periphery separating an exterior cover panel surface and an interior cover panel surface, said cover panel periphery partially attached to said undergarment main body such that said interior cover panel surface and said undergarment main body exterior surface together define a cover panel interior space, said cover panel partially detached from said undergarment main body providing access to said cover panel interior space; and
    a packaged sanitary absorbent article holder affixed to and disposed upon said interior surface of said cover panel, said packaged sanitary absorbent article holder being located within said cover panel interior space,
    wherein, said packaged sanitary absorbent article is retained away from undesirable contact with a body of a wearer of said undergarment by said packaged sanitary absorbent article and said undergarment main body thereby preventing undesirable direct contact of said article against said body of said wearer.

2. The undergarment of claim 1 wherein said packaged sanitary absorbent article holder is sized and configured to receive at least one tampon.

3. The undergarment of claim 1 wherein said packaged sanitary absorbent article holder is sized and configured to receive at least one sanitary napkin.

4. The undergarment of claim 1 wherein said packaged sanitary absorbent article holder comprises a pair of spaced-apart loops sized and configured to receive a tampon.

5. The undergarment of claim 1 wherein said packaged sanitary absorbent article holder comprises a scrolling pocket style, said scrolling pocket style being configured to receive a tampon.

6. The undergarment of claim 1 said cover panel further comprises a peripheral edge located proximate a front portion of each of said leg receiving openings.

7. The undergarment of claim 1 further comprising a closure mechanism carried by said packaged sanitary absorbent article holder and said interior cover panel surface.

8. The undergarment of claim 1 wherein said cover panel is attached to said exterior surface of said rear portion of said undergarment main body.

9. An undergarment adapted to discreetly store a packaged sanitary absorbent article, said undergarment comprising:
    a unitary liquid pervious undergarment main body constructed to be worn about a lower torso portion of a human body, said undergarment main body having interior and exterior surfaces and contiguous front and rear portions forming a waist-receiving opening and a pair of leg-receiving openings, said waist receiving opening defined by an upper edge of said undergarment main body;
    a cover panel attached to said exterior surface of said undergarment main body, said cover panel having a periphery separating exterior and an interior cover panel surfaces, said cover panel periphery partially attached to said undergarment main body such that said interior cover panel surface and said undergarment main body exterior surface together define a cover panel interior space, said cover panel partially detached from said undergarment main body providing access to said cover panel interior space; and a packaged sanitary absorbent article holder affixed to and disposed upon one of said interior surface of said cover panel and said exterior surface of said undergarment main body, said packaged sanitary absorbent article holder being located within said cover panel interior space, wherein, said packaged sanitary absorbent article is retained away from undesirable contact with a body of a wearer of said undergarment by said packaged sanitary absorbent article and said undergarment main body thereby preventing undesirable direct contact of said article against said body of said wearer.

10. The undergarment of claim 9 wherein said packaged sanitary absorbent article holder is sized and configured to receive at least one tampon.

11. The undergarment of claim 9 wherein said packaged sanitary absorbent article holder is sized and configured to receive at least one sanitary napkin.

12. The undergarment of claim 9 wherein said packaged sanitary absorbent article holder comprises a pair of spaced-apart loops sized and configured to receive a tampon.

13. The undergarment of claim 9 wherein said packaged sanitary absorbent article holder comprises a scrolling pocket style, said scrolling pocket style being configured to receive a tampon.

14. The undergarment of claim 9 said cover panel further comprises a peripheral edge located proximate a front portion of each of said leg receiving openings.

15. The undergarment of claim 9 further comprising a closure mechanism carried by said packaged sanitary absorbent article holder and said interior cover panel surface.

16. The undergarment of claim 9 wherein said cover panel is attached to said exterior surface of said rear portion of said undergarment main body.

17. An undergarment adapted to discreetly store a packaged sanitary absorbent article, said undergarment comprising:

a unitary liquid pervious undergarment main body constructed to be worn about a lower torso portion of a human body, said undergarment main body having interior and exterior surfaces and contiguous front and rear portions forming a waist-receiving opening and a pair of leg-receiving openings, said waist receiving opening defined by an upper edge of said undergarment main body;

a cover panel attached to said exterior surface of said front portion of said undergarment main body, said cover panel having a periphery separating exterior and an interior cover panel surfaces, said cover panel periphery partially attached to said undergarment main body such that said interior cover panel surface and said undergarment main body exterior surface together define a cover panel interior space, said cover panel partially detached to said undergarment main body providing access to said cover panel interior space; and a packaged sanitary absorbent article holder affixed to and disposed upon one of said interior surface of said cover panel and said exterior surface of said undergarment main body, said packaged sanitary absorbent article holder being located within said cover panel interior space, wherein, said packaged sanitary absorbent article is retained away from undesirable contact with a body of a wearer of said undergarment by said packaged sanitary absorbent article and said undergarment main body thereby preventing undesirable direct contact of said article against said body of said wearer.

18. The undergarment of claim 17 wherein said packaged sanitary absorbent article holder comprises a pair of spaced-apart loops sized and configured to receive a tampon.

19. The undergarment of claim 17 wherein said packaged sanitary absorbent article holder comprises a scrolling pocket style, said scrolling pocket style being configured to receive a tampon.

20. The undergarment of claim 17 said cover panel further comprises a peripheral edge located proximate a front portion of each of said leg receiving openings.

21. The undergarment of claim 17 further comprising a closure mechanism carried by said packaged sanitary absorbent article holder and said interior cover panel surface.

* * * * *